(12) United States Patent
Neumann

(10) Patent No.: US 11,823,786 B1
(45) Date of Patent: Nov. 21, 2023

(54) APPARATUS AND METHOD FOR ADJUSTING A USER NOURISHMENT SELECTION BASED ON NUTRIENT DIVERSITY

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/833,365

(22) Filed: Jun. 6, 2022

(51) Int. Cl.
*G16H 20/60* (2018.01)
*G16H 50/30* (2018.01)

(52) U.S. Cl.
CPC ............. *G16H 20/60* (2018.01); *G16H 50/30* (2018.01)

(58) Field of Classification Search
CPC .............................. G16H 20/60; G16H 50/30
USPC ......................................................... 705/2, 3
See application file for complete search history.

(56) References Cited

U.S. PATENT DOCUMENTS

| 10,553,316 | B1 | 3/2020 | Neumann | |
|---|---|---|---|---|
| 2019/0304000 | A1* | 10/2019 | Simpson | .......... G01N 33/48792 |
| 2022/0059214 | A1* | 2/2022 | Jung | ....................... G16H 50/30 |

OTHER PUBLICATIONS

Bowyer, R.C.E., Jackson, M.A., Pallister, T. et al. Use of dietary indices to control for diet in human gut microbiota studies. Microbiome 6, 77 (2018). https://doi.org/10.1186/s40168-018-0455-y (Year: 2018).*
"Machine Learning Classifiers—The Algorithms & How They Work" published on MonkeyLearn Dec. 14, 2020. retrieved from https://monkeylearn.com/blog/what-is-a-classifier/ (Year: 2020).*
Steck, H., Baltrunas, L., Elahi, E., Liang, D., Raimond, Y., & Basilico, J. (2021). Deep Learning for Recommender Systems: A Netflix Case Study. AI Magazine, 42(3), 7-18. https://doi.org/10.1609/aimag.v42i3.18140 (Year: 2021).*
Iwendi, Celestine, Khan, Suleman, Anajemba, Joseph Henry, Bashir, Ali Kashif ORCID logo and Noor, Fazal (2020) Realizing an Efficient IoMT-Assisted Patient Diet Recommendation System Through Machine Learning Model. IEEE Access, 8. pp. 28462-28474. (Year: 2020).*

* cited by examiner

*Primary Examiner* — Joshua B Blanchette
(74) *Attorney, Agent, or Firm* — CALDWELL INTELLECTUAL PROPERTY LAW

(57) ABSTRACT

An apparatus and method for adjusting a user nourishment selection based on nutrient diversity, the apparatus comprising at least a processor and a memory communicatively connected to the at least a processor, the memory containing instructions configuring the at least a processor to receive a proposed user selection relating to nourishment, wherein the proposed user selection comprises a plurality of ingredients, evaluate each ingredient of the plurality of ingredients, wherein evaluating each ingredient includes extracting at least a nutrient from each ingredient of the plurality of ingredients and calculating a nutrient biodiversity score for the at least a nutrient, optimize the plurality of ingredients as a function of each nutrient biodiversity score, and adjust the plurality of ingredients as a function of the optimization of the plurality of ingredients.

20 Claims, 6 Drawing Sheets

APPARATUS AND METHOD FOR ADJUSTING A USER NOURISHMENT SELECTION BASED ON NUTRIENT DIVERSITY

FIELD OF THE INVENTION

The present invention generally relates to the field of toxic loads. In particular, the present invention is directed to an apparatus and method for adjusting a user nourishment selection based on nutrient diversity.

BACKGROUND

Consuming a variety of foods with diverse nutrients increases diversity in the human microbiome and overall health.

SUMMARY OF THE DISCLOSURE

In an aspect, an apparatus for adjusting a user nourishment selection based on nutrient diversity is shown. The apparatus comprising at least a processor and a memory communicatively connected to the at least a processor, the memory containing instructions configuring the at least a processor to receive a proposed user selection relating to nourishment, wherein the proposed user selection comprises a plurality of ingredients, evaluate each ingredient of the plurality of ingredients, wherein evaluating each ingredient includes extracting at least a nutrient from each ingredient of the plurality of ingredients and calculating a nutrient biodiversity score for the at least a nutrient, optimize the plurality of ingredients as a function of each nutrient biodiversity score, and adjust the plurality of ingredients as a function of the optimization of the plurality of ingredients.

In another aspect, a method for adjusting a user nourishment selection based on nutrient diversity is presented. The method comprises receiving, at the at least a processor, a proposed user selection relating to nourishment, wherein the proposed user selection comprises a plurality of ingredients, evaluating, at the at least a processor, each ingredient of the plurality of ingredients, wherein evaluating each ingredient includes extracting at least a nutrient from each ingredient of the plurality of ingredients and calculating a nutrient biodiversity score for the at least a nutrient, optimizing, at the at least a processor, the plurality of ingredients as a function of each nutrient biodiversity score, and adjusting, at the at least a processor, the plurality of ingredients as a function of the optimization of the plurality of ingredients.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for adjusting a user nourishment selection based on nutrient diversity. Aspects of the present disclosure may include at least a processor and a memory communicatively connected to the at least a processor. Aspects of the present disclosure may include the memory containing instructions configuring the at least a processor to receive a proposed user selection relating to nourishment, wherein the proposed user selection comprises a plurality of ingredients. Aspects of the present disclosure may include evaluating each ingredient of the plurality of ingredients, wherein evaluating each ingredient includes extracting at least a nutrient from the ingredient and calculating a nutrient biodiversity score for the at least a nutrient. Aspects of the present disclosure may include optimizing the plurality of ingredients as a function of each nutrient biodiversity score. Aspects of the present disclosure may include adjusting the plurality of ingredients as a function of the optimization of the plurality of ingredients.

Figure 1:
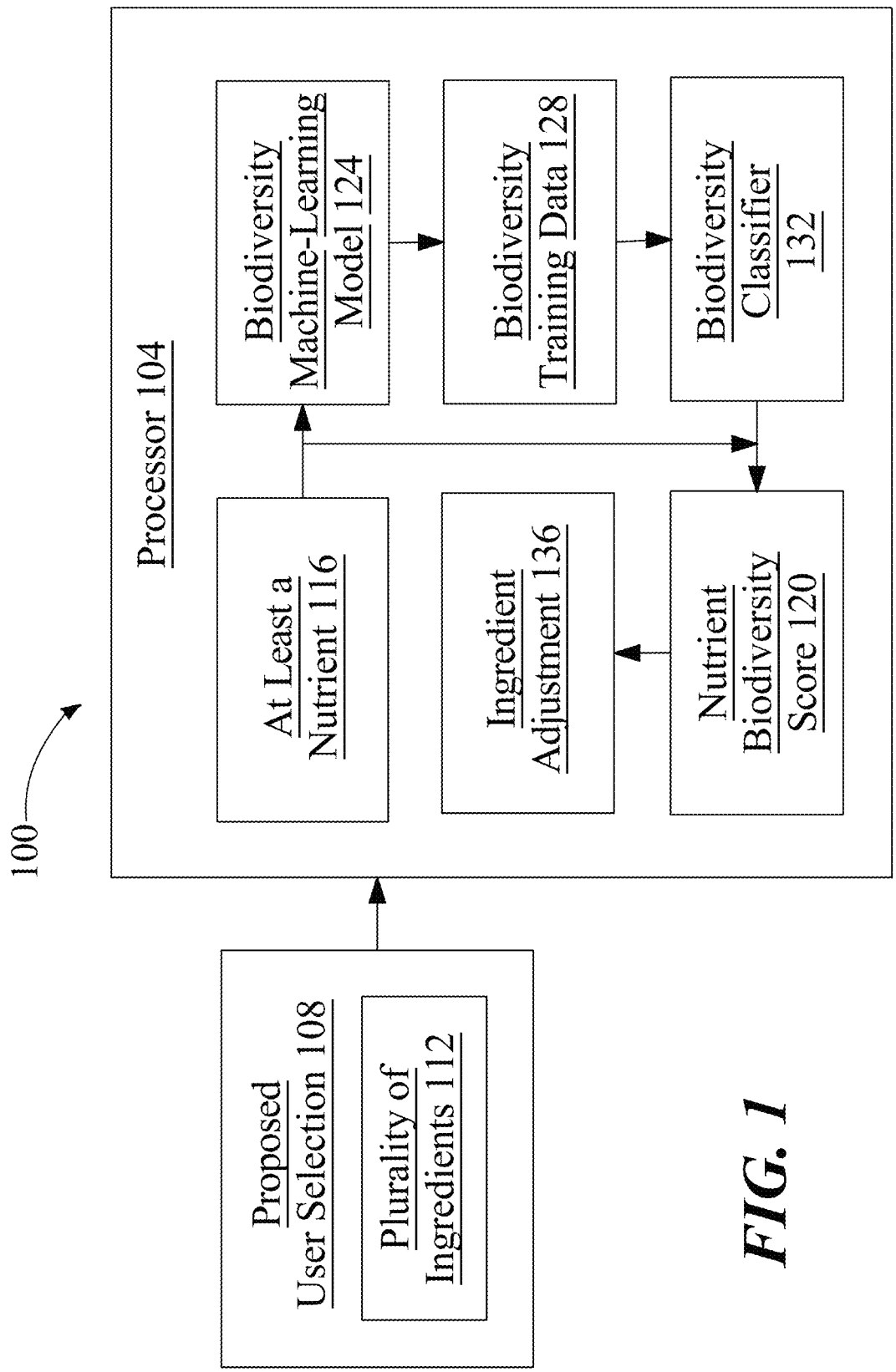
FIG. 1 is an exemplary embodiment of a block diagram of an apparatus for adjusting a user nourishment selection based on nutrient diversity.

Now referring to FIG. 1, an apparatus 100 for adjusting a user nourishment selection based on nutrient diversity is presented in the block diagram. Apparatus 100 may include at least a processor 104 and a memory communicatively connected to the at least a processor 104. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, a memory may contain instructions configuring the at least a processor 104 to perform various tasks. Apparatus 100 may include any computing device as described in this disclosure, including without limitation a microcontroller, microprocessor, digital signal processor (DSP) and/or system on a chip (SoC) as described in this disclosure. Apparatus 100 may include, be included in, and/or communicate with a mobile device such as a mobile telephone or smartphone. Apparatus 100 may include a single computing device operating independently, or may include two or more computing device operating in concert, in parallel, sequentially or the like; two or more computing devices may be included together in a single computing device or in two or more computing devices. Apparatus 100 may interface or communicate with one or more additional devices as described below in further detail via a network interface device. Network interface device may be utilized for connecting apparatus 100 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Apparatus 100 may include but is not limited to, for example, a computing device or cluster of computing devices in a first location and a second computing device or cluster of computing devices in a second location. Apparatus 100 may include one or more computing devices dedicated to data storage, security, distribution of traffic for load balancing, and the like. Apparatus 100 may distribute one or more computing tasks as described below across a plurality of computing devices of computing device, which may operate in parallel, in series, redundantly, or in any other manner used for distribution of tasks or memory between computing devices. Apparatus 100 may be implemented using a "shared nothing" architecture in which data is cached at the worker, in an embodiment, this may enable scalability of system 100 and/or computing device.

With continued reference to FIG. 1, apparatus 100 may be designed and/or configured to perform any method, method step, or sequence of method steps in any embodiment described in this disclosure, in any order and with any degree of repetition. For instance, apparatus 100 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Apparatus 100 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, at least a processor 104 is configured to receive a proposed user selection 108 relating to nourishment. A "user selection" as described in this disclosure, is data describing a user's preference in regard to any source of nourishment, including any food and/or beverage consumed by a human being. Proposed user selection 108 may indicate a user's like or dislike of an ingredient, a meal, a drink or beverage, and the like. Proposed user selection 108 may further include a recipe, meal, snack, or any sort of combination of nourishment ingredients that a user may consume. Proposed user selection 108 comprises a plurality of ingredients 112. A "plurality of ingredients" refers to a collection of food or substances that are combined to make a dish or recipe for a user to consume. For instance and without limitation, proposed user selection 108 may indicate that a user likes ingredients such as avocado, salmon, and jasmine rice, but the user dislikes black olives. In yet another non-limiting example, proposed user selection 108 may indicate that a user likes meals that include chicken alfredo, chicken parmesan, and spaghetti and meatballs, but the user dislikes meals that contain fish including fish tacos and pan sautéed cod. Proposed user selection 108 may indicate a user's eating patterns including the number of meals a user eats each day, the times of the day the user prefers to eat meals, meals a user skips or does not eat, number of snacks a user consumes each day and the like. Proposed user selection 108 may indicate a nutrient deficiency, which is where the microbiome of the user lacks an essential nutrient needed for growth. Proposed user selection 108 may indicate a user's cooking and meal preparation patterns, including if a user cooks meals at home, orders meal preparation kits, orders prepared foods, shops for groceries online or in person at a grocery store, eats at restaurants, and the like. Proposed user selection 108 may indicate a user's meal and ingredient source, such as if a user prefers ingredients that do not contain genetically modified organisms (GMOs), if a user prefers seafood that is wild caught and sustainable, if a user prefers free-range poultry, and/or if a user prefers organically sourced produce for example. Information pertaining to proposed user selection 108 may be stored in a database, as described herein with reference to FIG. 2. Furthermore, receiving proposed user selection 108 relating to nourishment may include receiving a user flavor preference. As used herein, "user flavor preference" is ingredients or nutrients the user prefers over other ingredients and nutrients. User flavor preference may, without indication, that the user's favorite type of fruit is strawberries, the user is allergic to spinach, the user does not like the taste of seafood, or anything similar.

Referring still to FIG. 1, proposed user selection 108 may be received as a function of a biological extraction. As used in this disclosure "biological extraction" is at least an element of user biological data. As used in this disclosure, "biological data" is data indicative of a person's biological state; biological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Biological extraction may include at least a marker associated with a biochemical status of an individual. As used in this disclosure a "marker" is a biochemical datum that may pertain to a biochemical status of an individual. For instance, and without limitation, the marker may include a particular set of biomarkers, test results, and/or biochemical information that is recognized in a given medical field as useful for identifying biochemical statuses of individuals within a relevant field. As a non-limiting example, and without limitation, marker describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. Biological extraction data may alternatively or additionally include any data used as a biological extraction as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference. Additionally or alternatively, biochemical profile 108 may be determined according to any processes used as a determination process as described in U.S. Nonprovisional application Ser. No. 16/502,835 filed Jul. 3, 2019 and titled "METHODS AND SYSTEMS FOR ACHIEVING VIBRANT CONSTITUTION BASED ON USER INPUTS", the entirety of which is referenced herein.

Still referring to FIG. 1, biological extraction may be identified as a function of one or more monitoring devices. As used in this disclosure "monitoring device" is an electronic device that is worn on the person of a user, such as without limitation close to and/or on the surface of the skin, wherein the device can detect, analyze, and transmit biochemical information concerning an individual. The monitoring device may include, without limitation, any device that further collects, stores, and analyzes data associated with a biochemical profile. The monitoring device my consist of, without limitation, near-body electronics, on-body electronics, in-body electronics, electronic textiles, smart watches, smart glasses, smart clothing, fitness trackers, body sensors, wearable cameras, head-mounted displays, body worn cameras, Bluetooth headsets, wristbands, smart garments, chest straps, sports watches, fitness monitors, and the like thereof. The monitoring device may include directed light monitoring devices such as spectrophotometric device at least identify concentrations of markers and/or identify one or more user biochemical statuses such as body mass index, fat percentage, water percentage, bone mass percentage, muscle mass percentage, and the like thereof. The monitoring device may include, without limitation, earphones, earbuds, headsets, bras, suits, jackets, trousers, shirts, pants, socks, bracelets, necklaces, brooches, rings, jewelry, AR HMDs, VR HMDs, exoskeletons, location trackers, and gesture control wearables. The monitoring device may include one or more medical devices that are operated by one or more informed advisors, wherein an informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like. As a non-limiting example, a medical device of a stethoscope, ultrasound device, MM device, PET scanner, CT scanner, X-ray device, electrocardiogram device, and the like thereof.

Moreover, and still referring to FIG. 1, biological extraction may include at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C(HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using any machine-learning and/or language processing module as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which, as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. Apparatus 100 may receive at least a physiological data from one or more other devices after performance; apparatus 100 may alternatively or additionally perform one or more assessments and/or tests to obtain at least a physiological data, and/or one or more portions thereof, on apparatus 100. For instance, at least physiological data may include or more entries by a user in a form or similar graphical user interface object; one or more entries may include, without limitation, user responses to questions on a psychological, behavioral, personality, or cognitive test. For instance, apparatus 100 may present to a user a set of assessment questions designed or intended to evaluate a current state of mind of the user, a current psychological state of the user, a personality trait of the user, or the like; apparatus 100 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS)

Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, firmicutes, Bacteroidetes, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, cryptosporidium EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, Mill, CT scan, ultrasound, standard barium follow-through examination, barium enema, barium with contract, Mill fluoroscopy, positron emission tomography 9PET), diffusion-weighted Mill imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example Firmicutes species, Bacteroidetes species, Proteobacteria species, Verrumicrobia species, Actinobacteria species, Fusobacteria species, Cyanobacteria species and the like. Archaea may include methanogens such as *Methanobrevibacter smithies*' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, Anaerotruncus colihominis, bacteriology, *Bacteroides vulgates, Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, Firmicutes to Bacteroidetes ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, Oxalobacter formigenes, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fulness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of apparatus 100 or may be a separate device in communication with apparatus 100.

Referring still to FIG. 1, at least a processor 104 is further configured to evaluate each ingredient of the plurality of ingredients 112. Evaluating each ingredient of the plurality of ingredients 112 includes extracting at least a nutrient 116 from the ingredient. Ingredients are nutrition elements, wherein a "nutrition element," as used in this disclosure, is an item that includes at least a nutrient 116 intended to be used and/or consumed by a user. A "nutrient," as used in this disclosure," is a biologically active compound substance whose consumption provides nourishment essential for growth and the maintenance of life in a microbiome. Types of at least a nutrient 116 may include, without limitation, carbohydrates, proteins, fats, vitamins, minerals, dietary fiber, water, or the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

Continuing to refer to FIG. 1, evaluating each ingredient of the plurality of ingredients 112 includes calculating a nutrient biodiversity score 120 for the at least a nutrient 116. A "nutrient biodiversity score" is data including any character, symbolic, and/or numerical data, reflecting the diversity of the nutrient compared to the user's current diet and health status; in other words, the score relays how diverse the nutrient is amongst the nutrients the user would normally eat in their diet. Nutrient biodiversity score 120 represents the effect of the at least a nutrient 116 on the diversity of a microbiome. Nutrient biodiversity score 120 may be transient and/or dynamic. Nutrient biodiversity score 120 may be updated based on one or more meals that a user consumed and/or is planning to consume. Nutrient biodiversity score 120 may be calculated by at least a processor 104 by retrieving information contained within performance character database 136. Nutrient biodiversity score 120 may be graded on a continuum, where a score of zero may indicate a user who is in extremely poor nutritional health while a score of 100 may indicate a user who is in excellent nutritional health. Nutrient biodiversity score 120 may be calculated from one or more factors that may be stored within performance character database 136 such as food intake, water intake, supplement intake, prescription medication intake, fitness practice, health goals, chronic health conditions, acute health conditions, spiritual wellness, meditation practice, stress levels, and the like.

With continued reference to FIG. 1, calculating a nutrient biodiversity score 120 may include the use of a biodiversity machine-learning model 124. Calculating nutrient biodiversity score 120 also includes retrieving at least a nutrient containing a logged biodiversity entry. At least a processor 104 may then generate a biodiversity machine-learning model 124, wherein the biodiversity machine-learning model utilizes the logged biodiversity entry as an input, and outputs the nutrient biodiversity. A "logged nourishment entry," as used in this disclosure, is any stored factor that is utilized to calculate a nutrient biodiversity score 120. A logged nourishment entry may include a user's daily water intake, a user's supplement intake, and the like as described below in more detail. A logged nourishment entry may include a nourishment behavioral target. A "nourishment behavioral target," as used in this disclosure, is a user behavior goal relating to nourishment possibilities. A behavior goal may include a desire to cook a certain number of meals at home each week, or a desire to only eat fast food a certain number of times each month. A behavior goal may be self-reported by a user, and a user's progress towards meeting the behavior goal may be calculated into a user's nutrient biodiversity score 120. For example, a user who continues to not achieve any progress towards a user's nourishment behavior target to eat fish at least three times each week may decrease a user's overall nutrient biodiversity score 120, while a user with the same nourishment behavior target and who does continuously eat fish three times each week may increase the user's overall nutrient biodiversity score 120. A behavior goal may relate to a food source, such as a desire to only go out to eat no more than three days each week and to eat the rest of a user's meals at home. A behavior goal may relate to a food option such as to only consume foods that do not contain genetically modified organisms, or to only consume foods that do not contain high fructose corn syrup. Nutrient biodiversity score 120 may be affected by, without limitation, seasonal nutrients, allergies, local nutrients, or the like.

Figure 2:
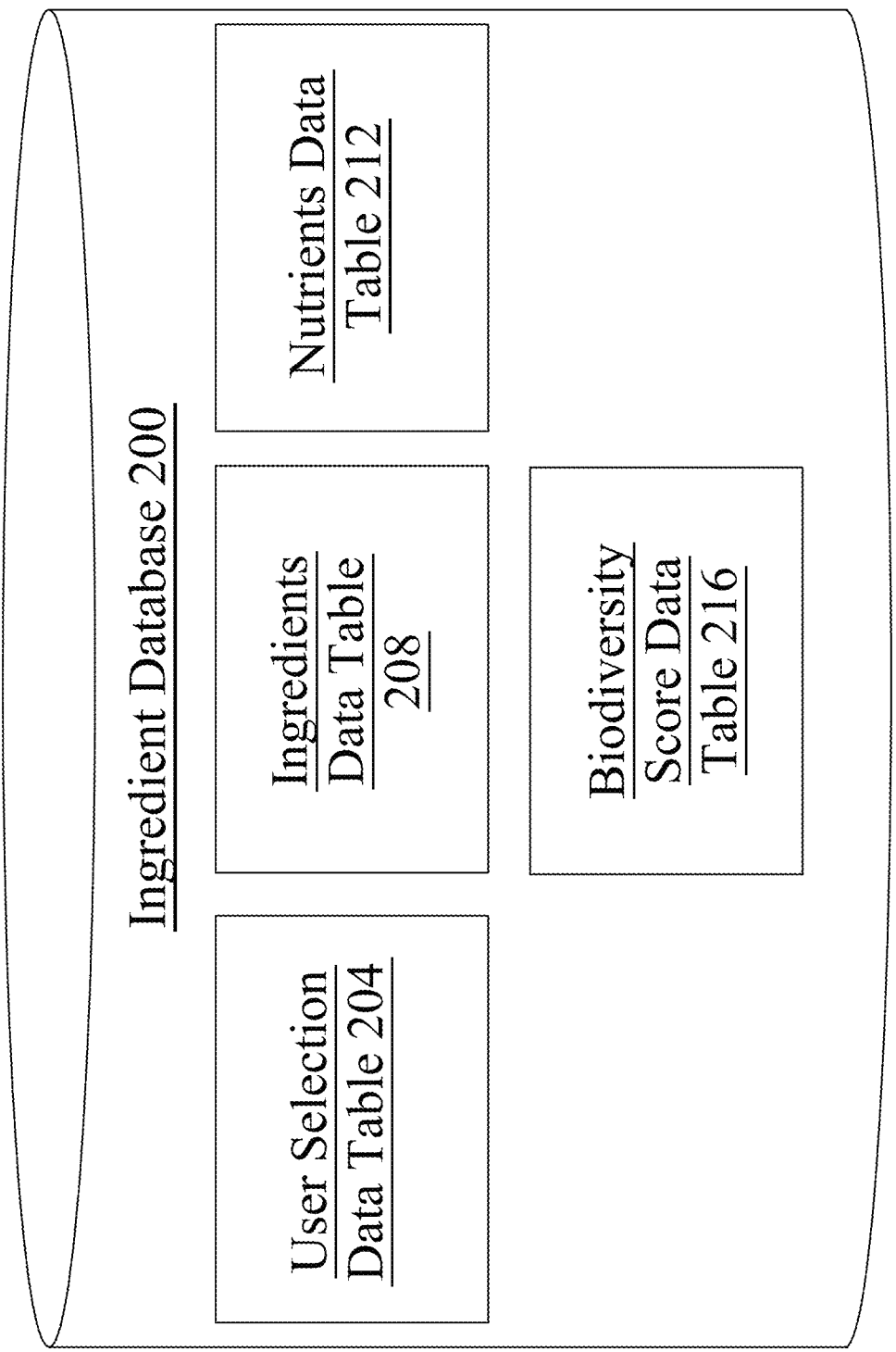
FIG. 2 is an exemplary embodiment of an ingredient database.

One or more logged nourishment entries may be stored in a database as described herein with reference to FIG. 2. At least a processor 104 may retrieve one or more elements of data containing a logged nourishment entry such as by generating a query, including any of the queries as described herein. At least a processor 104 generates a biodiversity machine-learning process. A "machine-learning process," as used in this disclosure, is a process that automatedly uses a body of data known as "training data" and/or a "training set" to generate an algorithm that will be performed by at least a processor 104 and/or a module to produce outputs given data provided as inputs; this is in contrast to a non-machine learning software program where the commands to be executed are determined in advance by a user and written in a programming language. As used herein, training data used to train biodiversity machine-learning model 124 is biodiversity training data 128. Biodiversity training data 128 may input any of the data described herein from proposed user selection relating to nourishment or a database, and outputs a biodiversity nutrient score. A "biodiversity machine-learning process," as used in this disclosure, is any machine-learning process that utilizes a logged nourishment entry as an input, and outputs a biodiversity nutrient score 120. "Training data," as used in this disclosure, is data containing correlations that a machine-learning process including a machine-learning algorithm and/or machine-learning process may use to model relationships between two or more categories of data elements. Training data may be formatted to include labels, for instance by associating data elements with one or more descriptors corresponding to categories of data elements. Training data may not contain labels, where training data may not be formatted to include labels. Biodiversity machine-learning process may be generated calculating one or more machine-learning algorithms and/or producing one or more machine-learning models.

With continued reference to FIG. 1, a machine-learning model may include one or more supervised machine-learning algorithms, which may include active learning, classification, regression, analytical learning, artificial neural network, backpropagation, boosting, Bayesian statistics, case-based learning, genetic programming, Kernel estimators, naïve Bayes classifiers, maximum entropy classifier, conditional random field, K-nearest neighbor algorithm, support vector machine, random forest, ordinal classification, data pre-processing, statistical relational learning, and the like. A machine-learning algorithm may include an unsupervised machine-learning algorithm, that is trained using training data that does not contain data labels. An unsupervised machine-learning algorithm may include a clustering algorithm such as hierarchical clustering, k-means clustering, mixture models, density based spatial clustering of algorithms with noise (DBSCAN), ordering points to identify the clustering structure (OPTICS), anomaly detection such as local outlier factor, neural networks such as autoencoders, deep belief nets, Hebbian learning, generative adversarial networks, self-organizing map, and the like. A machine-learning algorithm may include semi-supervised learning that may be trained using training data that contains a mixture of labeled and unlabeled data. A machine-learning algorithm may include reinforcement learning, self-learning, feature learning, sparse dictionary learning, anomaly detection, robot learning, association rules, and the like. A machine-learning algorithm may include generating one or more machine-learning models. A "machine-learning model," as used in this disclosure, is any mathematical representation of a relationship between inputs and outputs. A machine-learning model an artificial neural network, a decision tree, a support vector machine, regression analysis, Bayesian network, genetic algorithms, and the like.

Still referring to FIG. 1, calculating a nutrient biodiversity score may further include the use of a biodiversity classifier 132. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. Biodiversity classifier 132 may be configured to output at least a datum that labels or otherwise identifies a set of data that are clustered together, found to be close under a distance metric as described below, or the like. At least a processor 104 and/or another device may generate a biodiversity classifier 132 using a classification algorithm, defined as a processes whereby a at least a processor 104 derives a classifier from training data. Biodiversity classifier may receive at least a nutrient 116 as input and output a nutrient biodiversity score 120. Training data for biodiversity classifier 132 may include any of the inputs and outputs described above. Training data for biodiversity classifier 132 may include nutrients correlated to nutrient biodiversity scores. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, at least a processor 104 may be configured to generate a biodiversity classifier 132 using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(AB)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. At least a processor 104 may then calculate a likelihood table by calculating probabilities of different data entries and classification labels. At least a processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, at least a processor 104 may be configured to generate a biodiversity classifier 132 using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Classification may also occur as a function of a fuzzy inference system or doing some sort of average similarity score. "Fuzzy inference" is the process of formulating a mapping from a given input to an output using fuzzy logic. "Fuzzy logic" is a form of many-valued logic in which the truth value of variables may be any real number between 0 and 1. Fuzzy logic may be employed to handle the concept of partial truth, where the truth value may range between completely true and completely false. The mapping of a given input to an output using fuzzy logic may provide a basis from which decisions may be made and/or patterns discerned. A first fuzzy set may be represented, without limitation, according to a first membership function representing a probability that an input falling on a first range of values is a member of the first fuzzy set, where the first membership function has values on a range of probabilities such as without limitation the interval [0,1], and an area beneath the first membership function may represent a set of values within the first fuzzy set. A first membership function may include any suitable function mapping a first range to a probability interval, including without limitation a triangular function defined by two linear elements such as line segments or planes that intersect at or below the top of the probability interval. "Linguistic variables" may, in a non-limiting example, cover input value factors and the "defuzzified" output may represent a score or output indicating how likely a mission is to succeed or, via a functional output or threshold comparison, be used to make the "go/no go" determination. Linguistic variables may represent, for instance, degree of charge of batteries, external temperature, wind velocity, or any other variable that may affect a probability of successful completion of a flight. Combinations of input variables and/or member functions may be linked to and/or composed with output membership functions and/or functional output formulas such as TSK functions to generate a defuzzified probability of success, and/or score to be compared to a threshold. Any parameters, biases, weights or coefficients of membership functions may be tuned and/or trained using machine-learning algorithms as described in this disclosure. Fuzzy inferencing and logic is further described herein with reference to FIG. 3.

Still referring to FIG. 1, at least a processor 104 is also configured to optimize the plurality of ingredients 112 as a function of each nutrient biodiversity score 120. As used herein, "optimize" means to rearrange or rewrite to improve efficiency of processing. Optimizing plurality of ingredients 112 may include creating a list of the plurality of ingredients 112 and organizing list of the plurality of ingredients 112 based on the nutrient biodiversity score 120 of each ingredient. Organizing a list of plurality of ingredients 112 may include arranging them in order from lowest nutrient biodiversity score 120 to highest nutrient biodiversity score 120, or vice versa. Additionally, without limitation, organizing the list may include organizing the list from most present in the user's microbiome to least present or vice versa. List of ingredients may be organized in anyway in order to figure out which ingredients will increase the biodiversity of the user's microbiome.

Referring still to FIG. 1, at least a processor 104 is further configured to adjust the plurality of ingredients 112 as a function of the optimization of the plurality of ingredients 112. Ingredient adjustment 136 is an action of adjusting the plurality of ingredients 112. As used herein, an "adjustment" is any change in the original plurality of ingredients, including, without limitation, a change in amounts of ingredients, exchange of ingredients, or the like. Adjusting plurality of ingredients 112 may include replacing at least an ingredient of the plurality of ingredients 112. Also, adjusting plurality of ingredients 112 may further include maximizing the diversity of nutrients in the plurality of ingredients.

Furthermore and still referring to FIG. 1, at least a processor 104 may use a language processing module at any of the steps explained herein. A language processing module may include any hardware and/or software module. A language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams" where all sequences of n consecutive characters are considered. Any or all possible sequences of tokens or words may be stored as "chains", for example for use as a Markov chain or Hidden Markov Model.

A language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Still referring to FIG. 1, a language processing module and/or diagnostic engine may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Now referring to FIG. 2, an exemplary embodiment of an ingredient database 200 is presented. Ingredient database 200 may include any database as described above with reference to FIG. 1. Ingredient database 200 may be include a database. Database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Still referring to FIG. 2, in some embodiments, ingredient database 200 may include user selection data table 204. User selection data table 204 may include, but is not limited to, diet data, geographical data, exercise data, product usage data, product purchasing data, and the like. User selection data table 204 may include any of the physiological data as described above with reference to FIG. 1.

Still referring to FIG. 2, in some embodiments, ingredient database 200 may include ingredients data table 208. Ingredients data table 208 may include one or more ingredient used to comprise user selection 108. In some embodiments, ingredients data may include, without limitation, sources of ingredients, amounts of ingredients, types of ingredients, and the like.

Still referring to FIG. 2, in some embodiments, ingredient database 200 may include nutrients data table 212. Nutrients data table 212 may include, but is not limited to, types of nutrients in each ingredient, quantities of nutrients, frequency of consumption of nutrients, seasonal nutrients in the area, and the like. Plurality of ingredients 112 may be as described above with reference to FIG. 1.

Still referring to FIG. 2, in some embodiments, ingredient database 200 may include biodiversity score data table 216. Biodiversity score data table 216 may include, but is not limited to, levels of biodiversity in the user's microbiome, scores from previous user selections, predicted changes in biodiversity, and the like. Nutrient biodiversity score 120 may be as described above with reference to FIG. 1.

Figure 3:
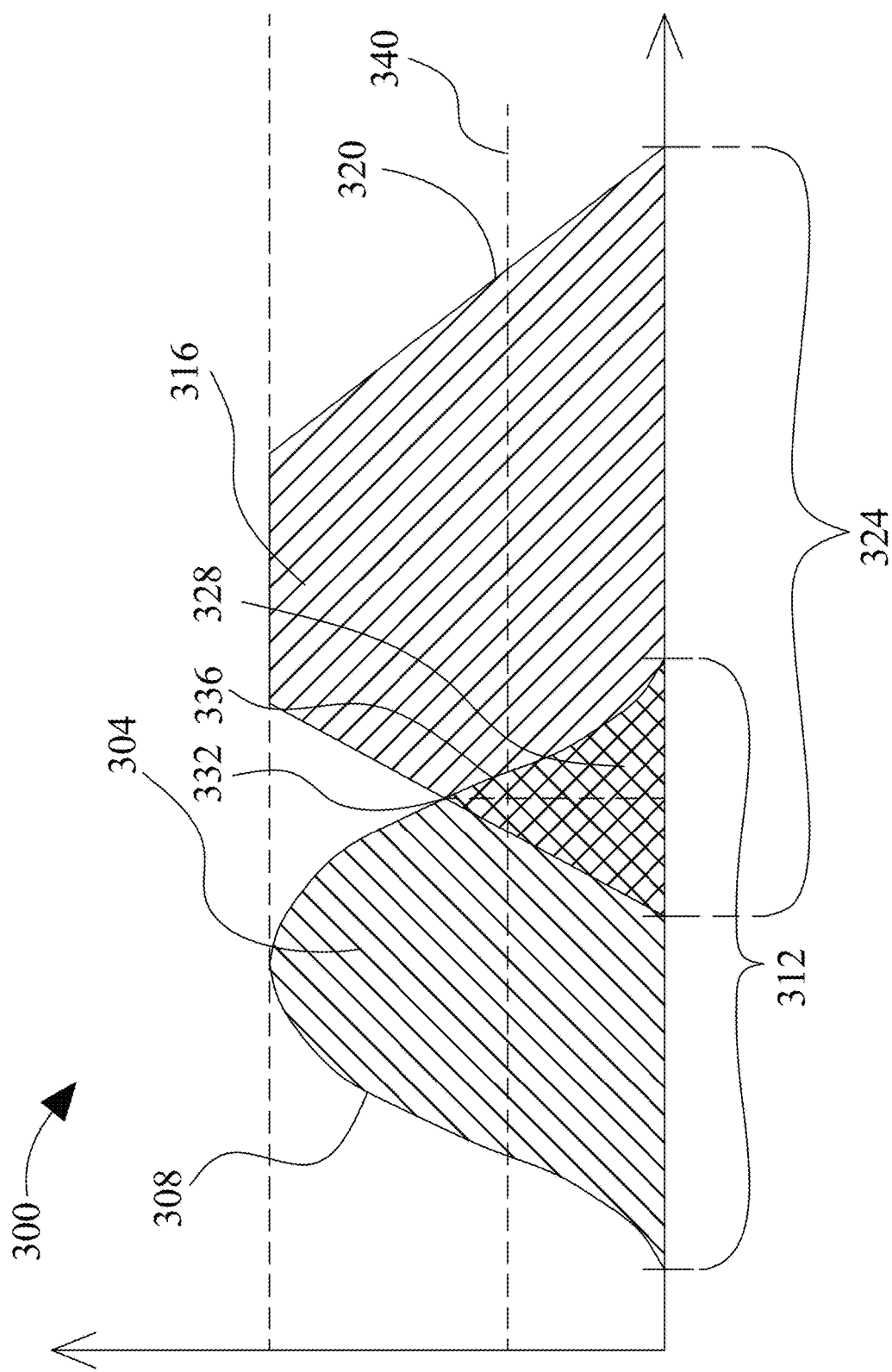
FIG. 3 is an exemplary embodiment of a fuzzy logic system.

Referring to FIG. 3, an exemplary embodiment of fuzzy set comparison 300 is illustrated. A first fuzzy set 304 may be represented, without limitation, according to a first membership function 308 representing a probability that an input falling on a first range of values 312 is a member of the first fuzzy set 304, where the first membership function 308 has values on a range of probabilities such as without limitation the interval [0,1], and an area beneath the first membership function 308 may represent a set of values within first fuzzy set 304. Although first range of values 312 is illustrated for clarity in this exemplary depiction as a range on a single number line or axis, first range of values 312 may be defined on two or more dimensions, representing, for instance, a Cartesian product between a plurality of ranges, curves, axes, spaces, dimensions, or the like. First membership function 308 may include any suitable function mapping first range 312 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 3, first fuzzy set 304 may represent any value or combination of values as described above, including output from one or more machine-learning models and articles of interest, a predetermined class, such as without limitation a toxic load quantifier. A second fuzzy set 316, which may represent any value which may be represented by first fuzzy set 304, may be defined by a second membership function 320 on a second range 324; second range 324 may be identical and/or overlap with first range 312 and/or may be combined with first range via Cartesian product or the like to generate a mapping permitting evaluation overlap of first fuzzy set 304 and second fuzzy set 316. Where first fuzzy set 304 and second fuzzy set 316 have a region 328 that overlaps, first membership function 308 and second membership function 320 may intersect at a point 332 representing a probability, as defined on probability interval, of a match between first fuzzy set 304 and second fuzzy set 316. Alternatively or additionally, a single value of first and/or second fuzzy set may be located at a locus 336 on first range 312 and/or second range 324, where a probability of membership may be taken by evaluation of first membership function 308 and/or second membership function 320 at that range point. A probability at 328 and/or 332 may be compared to a threshold 340 to determine whether a positive match is indicated. Threshold 340 may, in a non-limiting example, represent a degree of match between first fuzzy set 304 and second fuzzy set 316, and/or single values therein with each other or with either set, which is sufficient for purposes of the matching process; for instance, threshold may indicate a sufficient degree of overlap between an output from one or more machine-learning models and/or an article of interest and a predetermined class, such as without limitation a toxic load quantifier for combination to occur as described above. Alternatively or additionally, each threshold may be tuned by a machine-learning and/or statistical process, for instance and without limitation as described in further detail below.

Further referring to FIG. 3, in an embodiment, a degree of match between fuzzy sets may be used to classify an article of interest with a toxic load quantifier. For instance, if an article of interest has a fuzzy set matching a toxic load quantifier fuzzy set by having a degree of overlap exceeding a threshold, apparatus 100 may classify the article of interest as belonging to the toxic load quantifier fuzzy set. Where multiple fuzzy matches are performed, degrees of match for each respective fuzzy set may be computed and aggregated through, for instance, addition, averaging, or the like, to determine an overall degree of match.

Still referring to FIG. 3, in an embodiment, an article of interest may be compared to multiple toxic load quantifier fuzzy sets. For instance, an article of interest may be represented by a fuzzy set that is compared to each of the multiple toxic load quantifier fuzzy sets; and a degree of overlap exceeding a threshold between the article of interest fuzzy set and any of the multiple toxic load quantifier fuzzy sets may cause apparatus 100 to classify the article of interest as belonging to a toxic load quantifier fuzzy set. For instance, in one embodiment there may be two toxic load quantifier fuzzy sets, representing respectively a high toxic load quantifier fuzzy set and a moderate toxic load quantifier fuzzy set. A high toxic load quantifier fuzzy set may have a first fuzzy set; a moderate toxic load quantifier fuzzy set may have a second fuzzy set; and articles of interest may have an articles of interest fuzzy set. Apparatus 100, for example, may compare an article of interest fuzzy set with each of a high toxic load quantifier fuzzy set and a moderate toxic load quantifier fuzzy set, as described above, and classify an article of interest to either, both, or neither of a high toxic load quantifier fuzzy set or a moderate toxic load quantifier fuzzy set. Machine-learning methods as described throughout may, in a non-limiting example, generate coefficients used in fuzzy set equations as described above, such as without limitation $x$, $c$, and $\sigma$ of a Gaussian set as described above, as outputs of machine-learning methods. Likewise, an article of interest may be used indirectly to determine a fuzzy set, as an article of interest fuzzy set may be derived from outputs of one or more machine-learning models that take the article of interest directly or indirectly as inputs.

Still referring to FIG. 3, a processor may use a logic comparison program, such as, but not limited to, a fuzzy logic model to determine a toxic load quantifier. A toxic load quantifier may include, but is not limited to, low, average, high, and the like; each such toxic load quantifier may be represented as a value for a linguistic variable representing a toxic load quantifier or in other words a fuzzy set as described above that corresponds to a degree of toxic load as calculated using any statistical, machine-learning, or other method that may occur to a person skilled in the art upon reviewing the entirety of this disclosure. In other words, a given element of an article of interest may have a first non-zero value for membership in a first linguistic variable value such as "1" and a second non-zero value for membership in a second linguistic variable value such as "2". In some embodiments, determining a toxic load quantifier may include using a linear regression model. A linear regression model may include a machine learning model. A linear regression model may be configured to map data of an article of interest and/or user data, such as ingredients of an article of interest, to one or more toxic load quantifiers. A linear regression model may be trained using training data correlating articles of interest to toxic load quantifiers. A linear regression model may map statistics such as, but not limited to, toxic load impact magnitude, frequency of articles of interest of toxic load quantifiers, and the like. In some embodiments, determining a toxic load quantifier of an article of interest may include using a toxic load quantifier classification model. A toxic load quantifier classification model may be configured to input collected data and cluster data to a centroid based on, but not limited to, frequency of appearance, linguistic indicators of toxic elements, and the like. Centroids may include scores assigned to them such that elements of articles of interest may each be assigned a score. In some embodiments, a toxic load quantifier classification model may include a K-means clustering model. In some embodiments, a toxic load quantifier classification model may include a particle swarm optimization model. In some embodiments, determining a toxic load quantifier of an article of interest may include using a fuzzy inference engine. A fuzzy inference engine may be configured to map one or more article of interest data elements using fuzzy logic. In some embodiments, a plurality of entity assessment devices may be arranged by a logic comparison program into toxic load quantifier arrangements. A "toxic load quantifier arrangement" as used in this disclosure is any grouping of objects and/or data based on skill level and/or output score. This step may be implemented as described above in FIGS. 1-3 and below in FIG. 5. Membership function coefficients and/or constants as described above may be tuned according to classification and/or clustering algorithms. For instance, and without limitation, a clustering algorithm may determine a Gaussian or other distribution of questions about a centroid corresponding to a given toxic load level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Further referring to FIG. 3, an inference engine may be implemented according to input and/or output membership functions and/or linguistic variables. For instance, a first linguistic variable may represent a first measurable value pertaining to elements of an article of interest such as a degree of toxicity of an element of an article of interest, while a second membership function may indicate a degree of toxic load impact of a subject thereof, or another measurable value pertaining to an article of interest. Continuing the example, an output linguistic variable may represent, without limitation, a score value. An inference engine may combine rules, such as: "if the article of interest has 'high amounts of a toxic element' and the usage frequency is 'high'", the toxic load quantifier is 'high'"—the degree to which a given input function membership matches a given rule may be determined by a triangular norm or "T-norm" of the rule or output membership function with the input membership function, such as min (a, b), product of a and b, drastic product of a and b, Hamacher product of a and b, or the like, satisfying the rules of commutativity ($T(a, b)=T(b, a)$), monotonicity: ($T(a, b) \leq T(c, d)$ if $a \leq c$ and $b \leq d$), (associativity: $T(a, T(b, c))=T(T(a, b), c)$), and the requirement that the number 1 acts as an identity element. Combinations of rules ("and" or "or" combination of rule membership determinations) may be performed using any T-conorm, as represented by an inverted T symbol or "$\perp$" such as max(a, b), probabilistic sum of a and b ($a+b-a*b$), bounded sum, and/or drastic T-conorm; any T-conorm may be used that satisfies the properties of commutativity: $\perp(a, b)=\perp(b, a)$, monotonicity: $\perp(a, b) \leq \perp(c, d)$ if $a \leq c$ and $b \leq d$, associativity: $\perp(a, \perp(b, c))=\perp(\perp(a, b), c)$, and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

Further referring to FIG. 3, an article of interest to be used may be selected by user selection, and/or by selection of a distribution of output scores, such as 30% low toxic load quantifiers, 40% moderate toxic load quantifiers, and 30% high toxic load quantifiers or the like. Each ranking may be selected using an additional function such as a degree of toxicity as described above.

Figure 4:
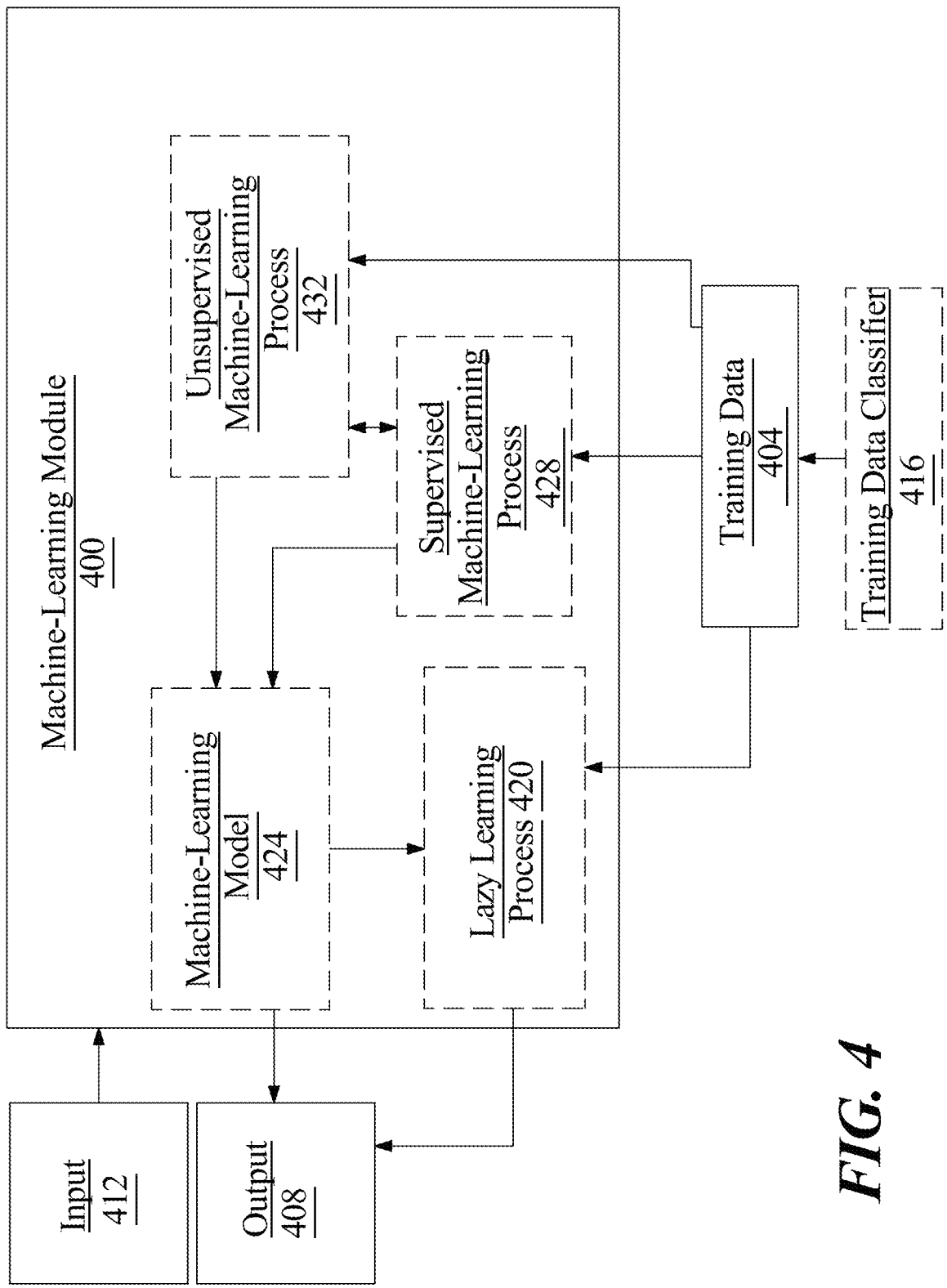
FIG. 4 is an exemplary embodiment of a block diagram of a machine leaning model.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example [describe inputs and outputs that might be used with invention].

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," as described herein, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to [something that characterizes a sub-population, such as a cohort of persons and/or other analyzed items and/or phenomena for which a subset of training data may be selected].

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include [input examples] as described above as inputs, [output examples] as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 5:
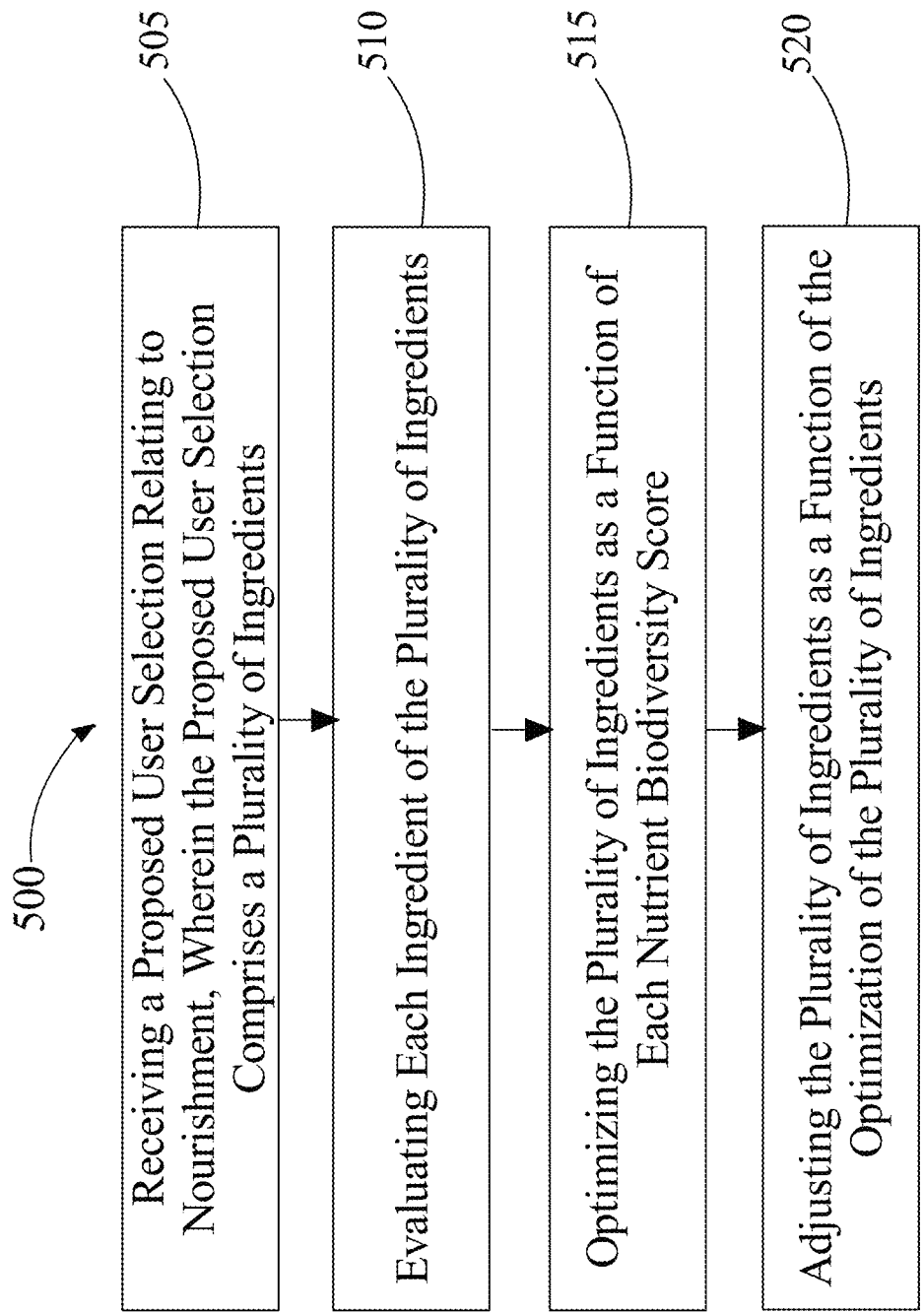
FIG. 5 is an exemplary embodiment of a flow diagram for a method for adjusting a user nourishment selection based on nutrient diversity.

Now referring to FIG. 5, a flow diagram for a method 500 for adjusting a user nourishment selection based on nutrient diversity is shown. Method 500 is performed by at least a processor 104. At least a processor 104 may be any of the processors or computing devices as described herein with reference to FIGS. 1 and 6.

Still referring to FIG. 5, at step 505, method 500 includes receiving, at the at least a processor 104, a proposed user selection 108 relating to nourishment, wherein proposed user selection 108 comprises a plurality of ingredients 112. Receiving proposed user selection 108 relating to nourishment may include receiving a user flavor preference. Proposed user selection 108 may be received as a function of a biological extraction. At least a processor 104 may be any of the processors or computing devices as described herein with reference to FIGS. 1 and 6. Proposed user selection 108 may be any of the data as described herein with reference to FIGS. 1 and 2. Plurality of ingredients 112 may be any of the ingredients as described herein with reference to FIGS. 1 and 2.

Still referring to FIG. 5, at step 510, method 500 includes evaluating, at the at least a processor 104, each ingredient of plurality of ingredients 112. At least a processor 104 may be any of the processors or computing devices as described herein with reference to FIGS. 1 and 6. Plurality of ingredients 112 may be any of the ingredients as described herein with reference to FIGS. 1 and 2.

Continuing to refer to FIG. 5, evaluating each ingredient includes extracting at least a nutrient 116 from each ingredient of the plurality of ingredients 112 and calculating a nutrient biodiversity score 120 for the at least a nutrient 116. Calculating a nutrient biodiversity score 120 may further include the use of a biodiversity machine-learning model 124. Calculating a nutrient biodiversity score 120 may further include the use of a nutrient classifier 132. Calculating nutrient biodiversity score 120 may comprise retrieving, at the at least a processor 104, at least a nutrient 116 containing a logged biodiversity entry and generating, at the at least a processor 104, a biodiversity machine-learning model 124, wherein the biodiversity machine-learning model utilizes the logged biodiversity entry as an input, and outputs the nutrient biodiversity score 120. Nutrient biodiversity score 120 represents the effect of the at least a nutrient 116 on the diversity of a microbiome. Plurality of ingredients 112 may be any of the ingredients as described herein with reference to FIGS. 1 and 2. At least a nutrient 116 may be any of the nutrients as described herein with reference to FIGS. 1 and 2. Nutrient biodiversity score 120 may be any of the scores as described herein with reference to FIGS. 1 and 2.

Still referring to FIG. 5, at step 515, method 500 includes optimizing, at the at least a processor 104, plurality of ingredients 112 as a function of each nutrient biodiversity score 120. Optimizing plurality of ingredients 112 includes creating, at the at least a processor 104, a list of the plurality of ingredients 112 and organizing, at the at least a processor 104, the list of the plurality of ingredients 112 based on each ingredient's biodiverse nutrient score 120. At least a processor 104 may be any of the processors or computing devices as described herein with reference to FIGS. 1 and 6. Plurality of ingredients 112 may be any of the ingredients as described herein with reference to FIGS. 1 and 2. Nutrient biodiversity score 120 may be any of the scores as described herein with reference to FIGS. 1 and 2.

Still referring to FIG. 5, at step 520, method 500 includes adjusting, at the at least a processor 104, plurality of ingredients 112 as a function of the optimization of the plurality of ingredients 112. Adjusting plurality of ingredients 112 may include replacing at least an ingredient of the plurality of ingredients 112. Adjusting plurality of ingredients 112 may include maximizing the diversity of nutrients in plurality of ingredients 112. At least a processor 104 may be any of the processors or computing devices as described herein with reference to FIGS. 1 and 6. Plurality of ingredients 112 may be any of the ingredients as described herein with reference to FIGS. 1 and 2.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
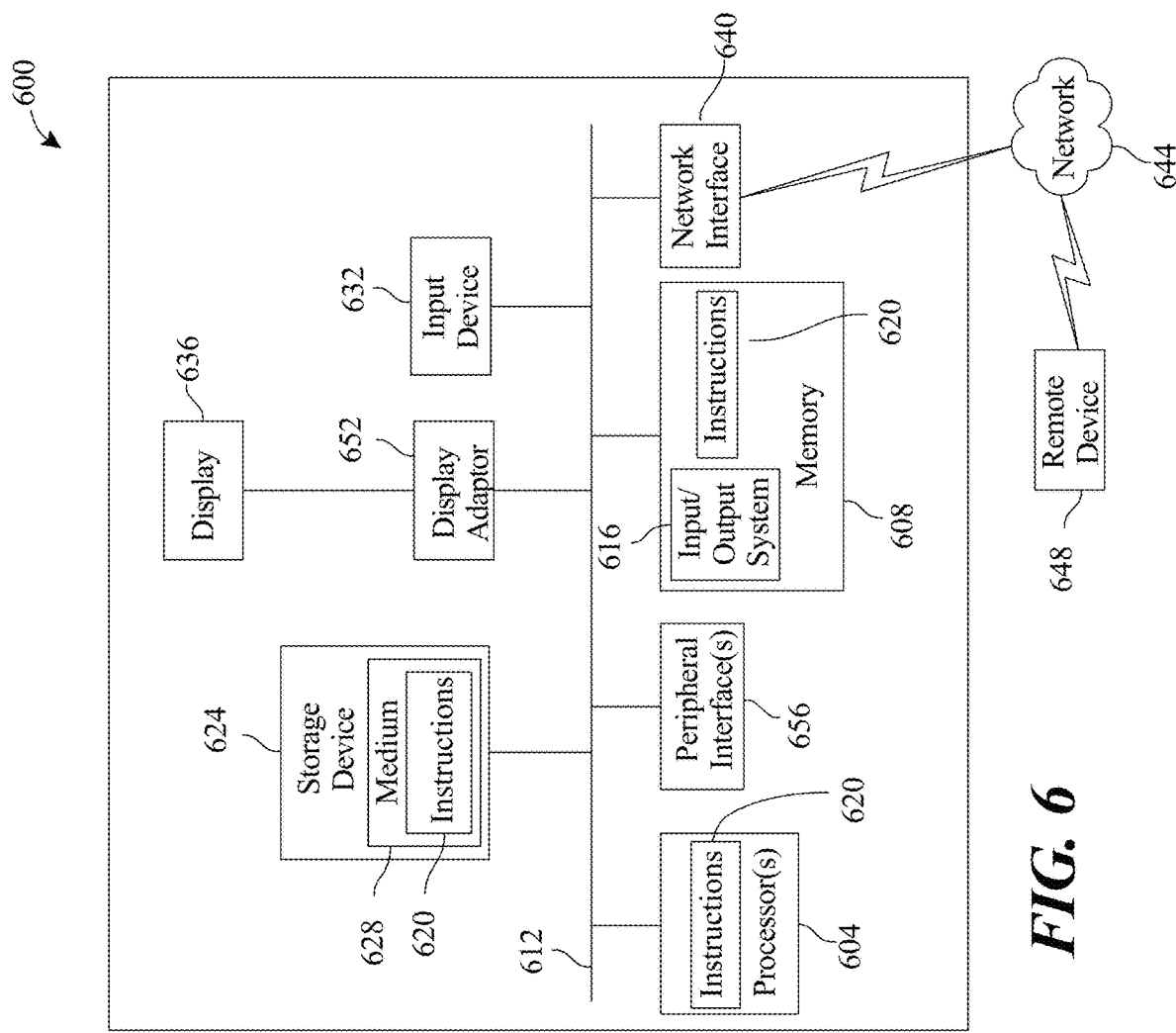
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for adjusting a user nourishment selection based on nutrient diversity, the apparatus comprising:
    a sensor configured to:
        detect hematological data of a user;
        store the hematological data as a function of at least a signal from the sensor; and
        transmit the hematological data;
    at least a processor; and
    a memory communicatively connected to the at least a processor, the memory configured to store the hematological data and containing instructions configuring the at least a processor to:
        receive a proposed user selection relating to nourishment, wherein the proposed user selection comprises a plurality of ingredients and the hematological data of the user;
        evaluate each ingredient of the plurality of ingredients, wherein evaluating each ingredient includes:
            extracting at least a nutrient from each ingredient of the plurality of ingredients; and
            calculating a nutrient biodiversity score associated with the user for the at least a nutrient, wherein calculating the nutrient biodiversity score comprises:
                classifying biodiversity training data, including a plurality of user selection data and a plurality of biodiversity nutrient score data, into categories using a fuzzy inference system by formulating mappings between elements of the plurality of user selection data and the plurality of biodiversity nutrient score data using fuzzy logic;
                training a biodiversity machine-learning model using the classified biodiversity training data; and
                generating the nutrient biodiversity score associated with the user using the biodiversity machine learning model by providing the at least a nutrient and the hematological data of the user as inputs to the trained biodiversity machine-learning model;
        optimize the plurality of ingredients as a function of each nutrient biodiversity score; and
        adjust the plurality of ingredients as a function of the optimization of the plurality of ingredients.

2. The apparatus of claim 1, wherein receiving the proposed user selection relating to nourishment includes receiving a user flavor preference.

3. The apparatus of claim 1, wherein calculating the nutrient biodiversity score further includes the use of a biodiversity classifier.

4. The apparatus of claim 1, wherein calculating the nutrient biodiversity score includes:
    retrieving at least a nutrient containing a logged biodiversity entry; and
    generating the nutrient biodiversity score by utilizeing the logged biodiversity entry as an input to the biodiversity machine-learning model.

5. The apparatus of claim 1, wherein the nutrient biodiversity score represents the effect of the at least a nutrient on a diversity of a microbiome.

6. The apparatus of claim 1, wherein optimizing the plurality of ingredients includes:
    creating a list of the plurality of ingredients; and
    organizing the list of the plurality of ingredients based on each ingredient of the plurality of ingredient's nutrient biodiversity score.

7. The apparatus of claim 1, wherein adjusting the plurality of ingredients includes replacing at least an ingredient of the plurality of ingredients.

8. The apparatus of claim 1, wherein adjusting the plurality of ingredients includes maximizing the diversity of nutrients in the plurality of ingredients.

9. The apparatus of claim 1, wherein the proposed user selection is received as a function of a biological extraction.

10. A method for adjusting a user nourishment selection based on nutrient diversity, the method comprises:
    detecting, at a sensor, hematological data of a user;
    storing, at the sensor, the hematological data as a function of at least a signal from the sensor; and
    transmitting, at the sensor, the hematological data;
    receiving, at a processor, a proposed user selection relating to nourishment, wherein the proposed user selection comprises a plurality of ingredients and the hematological data of the user;
    evaluating, at the processor, each ingredient of the plurality of ingredients, wherein evaluating each ingredient includes:
        extracting at least a nutrient from each ingredient of the plurality of ingredients; and calculating a nutrient biodiversity score associated with the user for the at least a nutrient, wherein calculating the nutrient biodiversity score comprises:

classifying biodiversity training data, including a plurality of user selection data and a plurality of biodiversity nutrient score data, into categories using a fuzzy inference system by formulating mappings between elements of the plurality of user selection data and the plurality of biodiversity nutrient score data using fuzzy logic;

training a biodiversity machine-learning model using the classified biodiversity training data; and generating the nutrient biodiversity score associated with the user using the biodiversity machine learning model by providing the at least a nutrient and the hematological data of the user as inputs to the trained biodiversity machine-learning model;

optimizing, at the processor, the plurality of ingredients as a function of each nutrient biodiversity score; and adjusting, at the processor, the plurality of ingredients as a function of the optimization of the plurality of ingredients.

11. The method of claim 10, wherein receiving the proposed user selection relating to nourishment includes receiving a user flavor preference.

12. The method of claim 10, wherein calculating the nutrient biodiversity score further includes the use of a biodiversity classifier.

13. The method of claim 10, wherein calculating the nutrient biodiversity score includes:

retrieving at least a nutrient containing a logged biodiversity entry; and generating the nutrient biodiversity score by utilizeing the logged biodiversity entry as an input to the biodiversity machine-learning model.

14. The method of claim 10, wherein the nutrient biodiversity score represents the effect of the at least a nutrient on a diversity of a microbiome.

15. The method of claim 10, wherein optimizing the plurality of ingredients includes:

creating a list of the plurality of ingredients; and organizing the list of the plurality of ingredients based on each ingredient of the plurality of ingredient's nutrient biodiversity score.

16. The method of claim 10, wherein adjusting the plurality of ingredients includes replacing at least an ingredient of the plurality of ingredients.

17. The method of claim 10, wherein adjusting the plurality of ingredients includes maximizing the diversity of nutrients in the plurality of ingredients.

18. The method of claim 10, wherein the proposed user selection is received as a function of a biological extraction.

19. The apparatus of claim 1, wherein:

the sensor is communicatively connected to the at least a processor and the memory;

the sensor comprises a wearable monitoring device that contacts the user during at least the detection of the hematological data of the user;

the hematological data comprises information relating to a nutrient deficiency of the user; and formulating the mappings between the elements of the plurality of user selection data and the plurality of biodiversity nutrient score data using fuzzy logic comprises determining a degree of overlap between at least a first fuzzy set representative of the elements of the plurality of user selection data and at least a second fuzzy set representative of the elements of the plurality of biodiversity nutrient score data.

20. The method of claim 10, wherein:

the sensor is communicatively connected to the at least a processor and the memory;

the sensor comprises a wearable monitoring device that contacts the user during at least the detection of the hematological data of the user;

the hematological data comprises information relating to a nutrient deficiency of the user; and formulating the mappings between the elements of the plurality of user selection data and the plurality of biodiversity nutrient score data using fuzzy logic comprises determining a degree of overlap between at least a first fuzzy set representative of the elements of the plurality of user selection data and at least a second fuzzy set representative of the elements of the plurality of biodiversity nutrient score data.

\* \* \* \* \*